US010201659B2

(12) United States Patent
Kaufmann et al.

(10) Patent No.: US 10,201,659 B2
(45) Date of Patent: Feb. 12, 2019

(54) ADMINISTRATION DEVICE FOR MIXING AN ACTIVE SUBSTANCE WITH A DILUTION LIQUID

(71) Applicant: TecPharma Licensing AG, Burgdorf (CH)

(72) Inventors: Nadine Kaufmann, Burgdorf (CH); Jürg Hirschel, Bern (CH); Markus Tschirren, Burgdorf (CH)

(73) Assignee: TecPharma Licensing AG, Burgdorf (CH)

( * ) Notice: Subject to any disclaimer, the term of this patent is extended or adjusted under 35 U.S.C. 154(b) by 1199 days.

(21) Appl. No.: 14/268,319

(22) Filed: May 2, 2014

(65) Prior Publication Data
US 2014/0243741 A1 Aug. 28, 2014

Related U.S. Application Data

(63) Continuation of application No. PCT/CH2012/000235, filed on Oct. 15, 2012.

(30) Foreign Application Priority Data

Nov. 3, 2011 (CH) ........................ 1767/11

(51) Int. Cl.
*A61M 5/20* (2006.01)
*A61M 5/32* (2006.01)
(Continued)

(52) U.S. Cl.
CPC ........ *A61M 5/2066* (2013.01); *A61M 5/3202* (2013.01); *A61M 5/326* (2013.01);
(Continued)

(58) Field of Classification Search
CPC .... A61M 5/20; A61M 5/2448; A61M 5/3213; A61M 5/3146; A61M 5/2066;
(Continued)

(56) References Cited

U.S. PATENT DOCUMENTS

| 3,825,003 A | 7/1974 | Kruck | |
|---|---|---|---|
| 8,251,947 B2 * | 8/2012 | KraMer | A61M 5/2066 604/82 |
| 2009/0292240 A1 * | 11/2009 | KraMer | A61M 5/2066 604/82 |

FOREIGN PATENT DOCUMENTS

| DE | 10203598 A1 | 8/2003 |
|---|---|---|
| GB | 2 319 184 | 5/1998 |

(Continued)

OTHER PUBLICATIONS

International Search Report dated Jan. 23, 2013 for PCT Application No. PCT/CH2012/00235 filed Oct. 15, 2012.

*Primary Examiner* — Kevin C Sirmons
*Assistant Examiner* — Tiffany Legette-Thompson
(74) *Attorney, Agent, or Firm* — Dorsey & Whitney LLP (57) ABSTRACT

An administration device comprises a container and a mixing device for mixing an active substance (in a first chamber) with a dilution liquid (in a second chamber). The container has a membrane seal at one end and is combined with a mixing device for mixing the active substance. The administration device has an injection needle unit with a distal needle portion facing away from the container for piercing the skin, and disposed opposite thereto is a proximal needle portion facing the membrane when the administration device is in the initial position, which is thrust through the membrane into the container in a mixing position. The administration device includes a protective sleeve arranged coaxially about the injection needle, movable from the initial position only in the proximal direction relative to the container. The protective sleeve can be non-rotatably connected to the container in the mixing position and rotated relative to the mixing device to perform mixing.

17 Claims, 8 Drawing Sheets (51) Int. Cl.
*A61M 5/24* (2006.01)
*A61M 5/31* (2006.01)

(52) U.S. Cl.
CPC ......... *A61M 5/2448* (2013.01); *A61M 5/3146* (2013.01); *A61M 5/3213* (2013.01); *A61M 2005/2073* (2013.01); *A61M 2005/2407* (2013.01); *A61M 2005/2451* (2013.01); *A61M 2005/2474* (2013.01); *A61M 2005/2488* (2013.01); *A61M 2005/3125* (2013.01); *A61M 2005/3247* (2013.01); *A61M 2205/581* (2013.01); *A61M 2205/582* (2013.01); *A61M 2205/583* (2013.01)

(58) Field of Classification Search
CPC ............ A61M 5/326; A61M 2205/581; A61M 2205/583; A61M 2205/582; A61M 2005/582; A61M 2005/3125; A61M 2005/2451; A61M 2005/2073; A61M 2005/2474; A61M 2005/3247; A61M 5/3202; A61M 5/284; A61M 5/285; A61M 5/286; A61M 5/19; A61M 2005/2407; A61M 2005/2488; A61M 2005/3117; A61M 39/045
USPC .......................................................... 604/88
See application file for complete search history.

(56) References Cited

FOREIGN PATENT DOCUMENTS

| | | |
|---|---|---|
| GB | 2 447 787 | 9/2008 |
| WO | WO 2008/122132 | 10/1988 |
| WO | WO 97/36624 | 10/1997 |
| WO | WO 03/057289 A1 | 7/2003 |
| WO | WO 2007/131013 | 11/2007 |
| WO | WO 2008/028304 | 3/2008 |
| WO | WO 2009/100549 | 8/2009 |
| WO | WO 2009/100550 | 8/2009 |
| WO | WO 2009/143640 A1 | 12/2009 |
| WO | WO2009/150078 A1 | 12/2009 |
| WO | WO 2010/072644 A1 | 7/2010 |

\* cited by examiner

ADMINISTRATION DEVICE FOR MIXING AN ACTIVE SUBSTANCE WITH A DILUTION LIQUID

CROSS-REFERENCE TO RELATED APPLICATIONS

This application is a continuation of International Patent Application No. PCT/CH2012/000235 filed Oct. 15, 2012, which claims priority to Swiss Patent Application No. CH 1767/11 filed Nov. 3, 2011, the entire contents of both of which are incorporated herein by reference.

BACKGROUND

The invention concerns an administration device, in particular, an administration device with a container and a mixing device for the mixing of an active substance with a dilution liquid in the container.

An administration device with a mixing device is known from WO2008/122132A1. With this administration device, the active substance is mixed with the dilution liquid by means of a relative rotation between a two-chamber cartridge, which holds an active substance and a dilution liquid, and a mixing device.

The disadvantage with the administration device in accordance with WO2008/122132A1 is that there is the danger that the user attempts to mix the active substance with the dilution liquid, before the needle was thrust into the two-chamber cartridge and consequently, an effective mixing is hindered, since, in particular, a gas formed during the mixing or a gas already contained in the two-chamber cartridge cannot escape. Moreover, there is the risk that the user may inject into the skin a fluid active substance that is only partially mixed.

In the following, the proximal direction with an administration device with an injection needle unit denotes the direction to the administration device and the distal direction, the direction to the injection needle unit.

SUMMARY

A goal of the device is to make available an administration device for the administration of a fluid active substance from a container, which ensures a previous thrust of the injection needle into the container and a mixing and/or priming of the active substance with the dilution liquid for the active substance.

The goal is attained by the administration device in accordance with Claim 1. Advantageous embodiments of such an administration device can be deduced from the dependent claims.

The device is based on an administration device for the administration of a fluid active substance from a container with at least one chamber with an active substance and a second chamber with a dilution liquid for the active substance. The container can be a cartridge, in which the active substance and the dilution liquid are directly held, or a cartridge holder, which comprises a cartridge with the active substance and the dilution liquid.

The container also has a membrane for sealing at one end. Preferably, the first chamber of the container can be limited by a first stopper and the second chamber, by the first and a second stopper. The chambers can be connected, via a bypass, in one wall, so as to make possible a mixing of the active substance with the dilution liquid.

Moreover, the administration device comprises a mixing device for the mixing of the active substance with the dilution liquid for the active substance. The mixing device can provide a sealing with respect to the second stopper. By a movement of the container relative to the mixing device, the second stopper and the first stopper can be pushed within the container as a result of the transfer of the force of the dilution liquid in the second chamber, until the first stopper has reached the area of the bypass. With additional movement of the container, relative to the mixing device, the second stopper is moved relative to the container, so that the dilution liquid arrives at the first chamber through the bypass and is mixed with the active substance. The mixing device can comprise a drive element, in particular, a piston rod, for the mixing of the active substance with the dilution liquid and for the administration of the mixed product, and a housing to hold the piston rod. During the mixing operation, the container can move axially, relative to the piston rod and the housing, and can preferably rotate. The container can be preferably thrust radially into the administration device, between the piston rod and the housing. The piston rod can be designed as a toothed rod or as a threaded rod and can be actuated manually as well as be driven by an electrical or mechanical drive, in particular, a spring.

The mixing device can thus be part of an administration mechanism of the administration device, wherein the container can be uncoupled from the administration mechanism, so as to couple a new container, after the old emptied container was disposed of. The administration mechanism can also provide a release knob and the administration mechanism is activated by its actuation, so that a mixed active substance from the container can be injected into the skin with an injection needle unit installed on the administration device. Furthermore, the administration device can comprise another safety device, which ensures that an injection can be carried out only after a complete mixing and/or priming of the active substance with the dilution liquid. To this end, the administration mechanism can have a blocking unit, which prevents the actuation of the release knob if the blocking device is in the blocking position. The blocking device can be moved from the blocking position into a release position, in which the release knob can be actuated for the administration of the mixed active substance. By rotating the container, relative to the mixing device, it is possible to move the blocking device from the blocking position to the release position. Therefore, by rotating the container, the administration device can be released and the administration mechanism can be released with the release knob. Such a blocking unit is described in WO2009/100550A1. WO2009/100550A1 is hereby completely assumed, by reference, into the document under consideration.

In one embodiment, the piston rod can also be designed in such a manner that it comprises a holding device, which holds the cartridge in a cartridge holder, in a defined position, relative to the housing. This arrangement can prevent too large a clearance between the individual components of the administration device and ensure a precise mode of functioning of the administration device. Such an arrangement is described in WO2009/100549A1, wherein WO2009/100549A1 is hereby completely incorporated by reference into this document.

Moreover, the administration device comprises an injection needle unit, which has a distal needle portion, turned away from the container, for piercing the skin, and a proximal needle portion, which lies opposite, facing the membrane, in an initial position of the administration device and which is thrust through the membrane into the container in a mixing position. If the proximal needle portion is thrust through the membrane into the container, the proximal needle portion can bring about a fluid connection with the container. Thus, during the mixing of the active substance with the dilution liquid, a formed gas or a gas already contained in the container can escape, during the mixing operation and/or the priming operation, through the injection needle of the injection needle unit.

The injection needle unit can be designed as a safety needle unit, which comprises a protective shield, which, during the injection into the skin, can be moved from a distal position, in which the protective shield surrounds the distal needle portion for the piercing of the skin, into a proximal position, in which the distal needle portion is exposed. After the injection, the protective shield can again go to a distal position, in which the protective shield is locked so that it cannot be detached, so as to prevent another injection with the injection needle unit used. Such an injection needle unit is described in WO2008/028394A1, wherein WO2008/028304A1 is hereby completely incorporated by reference into this document.

The administration device also comprises a protective sleeve, which can be arranged coaxially around the injection needle unit and which, in the initial position, relative to the container, with the injection needle unit, held by the protective sleeve, can be moved in the proximal direction, in particular, only in the proximal direction.

According to another aspect of the device under consideration, the protective sleeve can be rotated, in the initial position, relative to the container.

Moreover, in the mixing position, the protective sleeve can be connected with the container so it cannot rotate and so it can rotate relative to the mixing device, so as to mix the active substance with the dilution liquid for the active substance. A torque transfer from the protective sleeve to the container can be carried out directly via a detachable connection between the protective sleeve and the container or, indirectly, via a torque transfer means, in particular, via a sleeve, wherein the torque transfer means can enter into a detachable connection with the protective sleeve and/or the container. Before the nonrotating connection between the protective sleeve and the container can be brought about in the mixing position, at least the proximal needle portion of the injection needle unit must be thrust through the membrane into the container.

Preferably, a sleeve, in particular, a guide sleeve, can be situated between the injection needle unit and the protective sleeve. The guide sleeve can be connected firmly and axially on a proximal end with the container. Preferably, the guide sleeve can rotate, relative to the container. The connection between the guide sleeve and the container can be brought about by form locking or force locking. With particular preference, a recess can be provided in the guide sleeve, which interacts with a projection that protrudes to the outside and is located on the container, in particular, a surrounding wedge toward the outside, in such a way that an axially firm and preferably rotatable connection between the guide sleeve and the container can be brought about. The projection of the container can lock into the recess of the guide sleeve. In an alternative embodiment, it is possible to lock a projection provided on the guide sleeve, in particular, a surrounding wedge, into a recess provided on the container.

In accordance with the device, the guide sleeve can be advantageously rotated, relative to the container, in the initial position or in the mixing position. Furthermore, the protective sleeve can be stationary, relative to the guide sleeve, in the initial position or in the mixing position.

Moreover, the injection needle unit can be preferably held so it can move axially in the guide sleeve. The injection needle unit can be held so it can move axially in the guide sleeve, in such a way, that the proximal needle portion of the injection needle unit, in the initial position of the administration device, is opposite, facing the membrane, and wherein, the proximal needle portion of the injection needle unit, in the mixing position, is thrust through the membrane into the container.

Preferably, the protective sleeve can have a locking element that can be clamped, which, in the initial position, interacts with the guide sleeve, in such a way, that the protective sleeve with the injection needle unit held therein can be moved, relative to the container, in the proximal direction, in particular, only in the proximal direction. The locking element can be designed so it can be clamped in an elastic manner. The locking element can have the shape of a flap, in particular, as a bendable or bending-elastic flap. Preferably, the locking element, shaped as one piece on the protective sleeve, or the locking element, placed on the protective sleeve, can swivel radially, relative to the protective sleeve, or be radially and elastically deformable, relative to the protective sleeve. Preferably, the locking element can be, in the initial position, in a stop contact with the guide sleeve, and can prevent a relative movement of the protective sleeve to the guide sleeve or to the injection needle unit or to the container in the distal direction. Alternatively, the protective sleeve, in the initial position, can first be moved, relative to the guide sleeve, in the distal direction, until an additional relative movement in the distal direction is prevented by a stop contact between the locking element and the guide sleeve. Preferably, the guide sleeve can have a recess which is designed, in such a way, that a relative movement of the protective sleeve of the protective sleeve to the guide sleeve is permitted in the proximal direction and is prevented in the distal direction.

A stop surface of the locking element and a counter-surface of the recess of the guide sleeve form the stop contact between the locking element of the protective sleeve and the recess of the guide sleeve.

In the initial position, the protective sleeve can be held firmly and axially, relative to the guide sleeve, via a force- or form-locking connection, in particular, a groove/cam connection; in particular, it can be held firmly and axially in the proximal direction. The user can apply a force in the proximal direction which exceeds the holding force of the groove/cam connection, against the protective sleeve. The groove/cam connection can be loosened and the protective sleeve held with the injection needle unit can be moved, relative to the container, in the proximal direction.

Depending on the arrangement of the groove/cam connection, relative to the locking element of the protective sleeve and to the recess of the guide sleeve, a relative movement may be at least partially possible, in the initial position, between the protective sleeve and the guide sleeve, in the distal direction, until the locking element arrives at the stop contact with the recess. In the stop contact, between the locking element and the recess, the protective sleeve cannot be moved in the distal direction, relative to the guide sleeve. The protective sleeve cannot be removed from the injection needle unit.

Furthermore, the locking element of the protective sleeve can interact, in the mixing position, with the guide sleeve, in such a way, that the protective sleeve can be moved, relative to the container, in the distal direction.

In one embodiment of the device, the guide sleeve can have a guide mechanism, wherein the locking element of the protective sleeve can be guided along the guide mechanism. The guide mechanism can have a ramp on one end of the guide and a steep front edge on the other end of the guide. In the initial position, the locking element can impact, with a stop surface, against the front edge of the guide mechanism. The locking element can thus form a stop and the front edge of the guide mechanism, a counterstop. The locking element of the protective sleeve can be brought to a mixing position, via a piercing position, wherein the proximal needle portion of the injection needle pierces the membrane. In the mixing position, the locking element can slide over the ramp-like slope. By a rotation of the protective sleeve, relative to the guide sleeve, the administration device can arrive at the mixing position. The protective sleeve can be moved, with the locking element in the distal direction, relative to the guide sleeve or to the injection needle unit or to the container, only if a rotational movement of the protective sleeve with the locking element has taken place, relative to the guide sleeve. In the mixing position, the protective sleeve can be removed from the injection needle unit.

In one embodiment of the device, the locking element of the protective sleeve can be sufficiently moved in the proximal direction, relative to the guide sleeve, so as to attain the mixing position, until, on the one hand, the proximal needle portion of the injection needle unit has pierced the membrane and until, on the other hand, the locking element has slid over the proximal end of the guide sleeve and has relaxed, in particular, has relaxed in an elastic manner. The locking element can then protrude into a recess of the container or into a recess formed by the proximal end of the guide sleeve and a shoulder of the container or between projections, in particular, ribs, placed on the container. If the protective sleeve is moved, relative to the guide sleeve or to the injection needle unit or to the container, in the distal direction, the locking element of the protective sleeve is pretensioned by the guide sleeve; in particular, it is elastically pretensioned and can then slide over the guide sleeve and its recess. The protective sleeve can, therefore, be removed from the injection needle unit.

In one embodiment, the nonrotary connection between the protective sleeve and the container can be brought about, in the mixing position, by an intrusion between the container, in particular, the projection provided on the container, and a snap arm, which is located on the guide sleeve. On the guide sleeve, several snap arms can be provided, and on the container, several projections. The snap arm placed on the guide sleeve can form the torque transfer means. The guide sleeve can intrude in a nonrotary connection with the protective sleeve—in particular, a connection which does not rotate in a rotary direction. The guide sleeve, which is connected in a nonrotary manner with the protective sleeve, can transfer a rotating movement of the protective sleeve to the container by means of the snap arm provided on the guide sleeve.

If the protective sleeve is moved, relative to the container in the proximal direction, with the injection needle unit, held therein, the protective sleeve can slide over the guide sleeve and place the snap arm under tension, radially inwards. The snap arm can be pretensioned, radially inwards, in the piercing position and in the mixing position, in particular, elastically pretensioned. Preferably, the snap arm can act against the projection placed on the container, in the mixing position, and forms the intrusion between the container and the snap arm of the guide sleeve. The intrusion is used to bring about a nonrotary connection, in particular, a connection that does not rotate in a rotary direction, via the snap arm, between the protective sleeve and the container. If the user takes hold of the protective sleeve and rotates it relative to the mixing device, the container can be rotated, via the snap arm of the guide sleeve, relative to the mixing device, so as to mix the active substance with the dilution liquid for the active substance in the container. After the mixing operation has ended, the administration device can also be primed with another relative rotation between the container and the mixing device. A gas contained in the container and/or in the injection needle is thereby expelled, so that the administration device is ready for the injection into the skin.

In order to arrive at the mixing position, the protective sleeve, connected with the guide sleeve, in a manner that does not rotate, at least in one rotary direction, must preferably be rotated for the moment, before the snap arm placed on the guide sleeve acts against the projection placed on the container and brings about the intrusion between the container and the snap arm. In a particularly preferred embodiment, the protective sleeve must, for the moment, be rotated with the locking element, relative to the guide sleeve, so that the locking element is guided along the guide mechanism of the guide sleeve, until a connection between the locking element and the guide sleeve, which does not rotate in at least one rotary direction, is formed. With a further rotation of the protective sleeve, the locking element takes along the guide sleeve by means of the stop contact between the locking element and the guide mechanism, until the snap arm of the guide sleeve strikes on a projection provided on the container and takes along the container.

The user can thus also rotate the container, via the guide sleeve, relative to the mixing device by means of a rotation of the protective sleeve, relative to the mixing device, and bring about an effective mixing of the active substance with the dilution liquid. In particular, the user can radially screw the container, via the guide sleeve, into the administration device, between the housing and the drive element, in particular, the piston rod, by rotating the protective sleeve, relative to the mixing device, wherein the drive element, in particular, the piston rod, acts on the second stopper and brings about a mixing operation and/or priming operation.

In one embodiment, the nonrotary connection between the protective sleeve and the container can be brought about in the mixing position by an intrusion between the container and the protective sleeve or the locking element of the protective sleeve. The protective sleeve can move axially, relative to the guide sleeve, in the proximal direction. In the mixing position, the locking element or a part of the protective sleeve can protrude into a recess of the container or into a recess formed by the proximal end of the guide sleeve and a shoulder of the container or between projections placed on the container, especially, ribs, and strike against a projection provided on the container, especially, a rib, or against a stop surface surrounding the recess, and thus bring about the intrusion between the container and the protective sleeve or the locking element. In the mixing position, a connection that does not rotate, at least in one rotary direction, is brought about between the protective sleeve and the container. The locking element or the part of the protective sleeve can essentially extend, relaxed or elastically relaxed, into the recess of the container or into the recess formed by the proximal end of the guide sleeve and a shoulder of the container, or between projections placed on the container, especially, ribs.

Preferably, in the mixing position, the intrusion between the container and the protective sleeve or the locking element can be formed in such a way that, for the moment, the protective sleeve must be rotated, relative to the container, before the locking element or a part of the protective sleeve interferes with the container.

By a rotation of the protective sleeve, relative to the mixing device, the container can be rotated radially, relative to the mixing device; in particular, relative to the administration device, it can be screwed in between a housing and the piston rod. The mixing operation and/or the priming operation can thus be effectively accomplished.

The intrusion between the container and the snap arm of the protective sleeve as well as the intrusion between the locking element or the part of the protective sleeve can also be formed by another form-locking and/or force-locking intrusion. The intrusion can be a ribbed connection, groove/wedge connection, pin/borehole connection, stop connection, or snap connection.

Preferably, the administration device can have an indicating device, which comprises at least a first indication for the marking of a position of the container, relative to the mixing device, after ending the mixing operation and a second indication for the marking of a position of the container, relative to the mixing device, after ending the priming operation. To this purpose, a visual, acoustic, or tactile indicating device can be provided on the administration device, in particular, on the container, which indicates the position of the container, relative to the mixing device. Furthermore, locking positions can be provided for the indication of the individual position with the individual steps of the preparation of the administration device, such as the mixing and priming, which are formed by a reverse lock, by means of which it is no longer possible to remove the container, contrary to its introduction direction, from the housing.

BRIEF DESCRIPTION OF THE DRAWINGS

The device is described below on several figures. The features hereby disclosed refine the device advantageously, individually and in combination. The figures show the following.

DETAILED DESCRIPTION

Figures 1A, 1B, 2, 3:
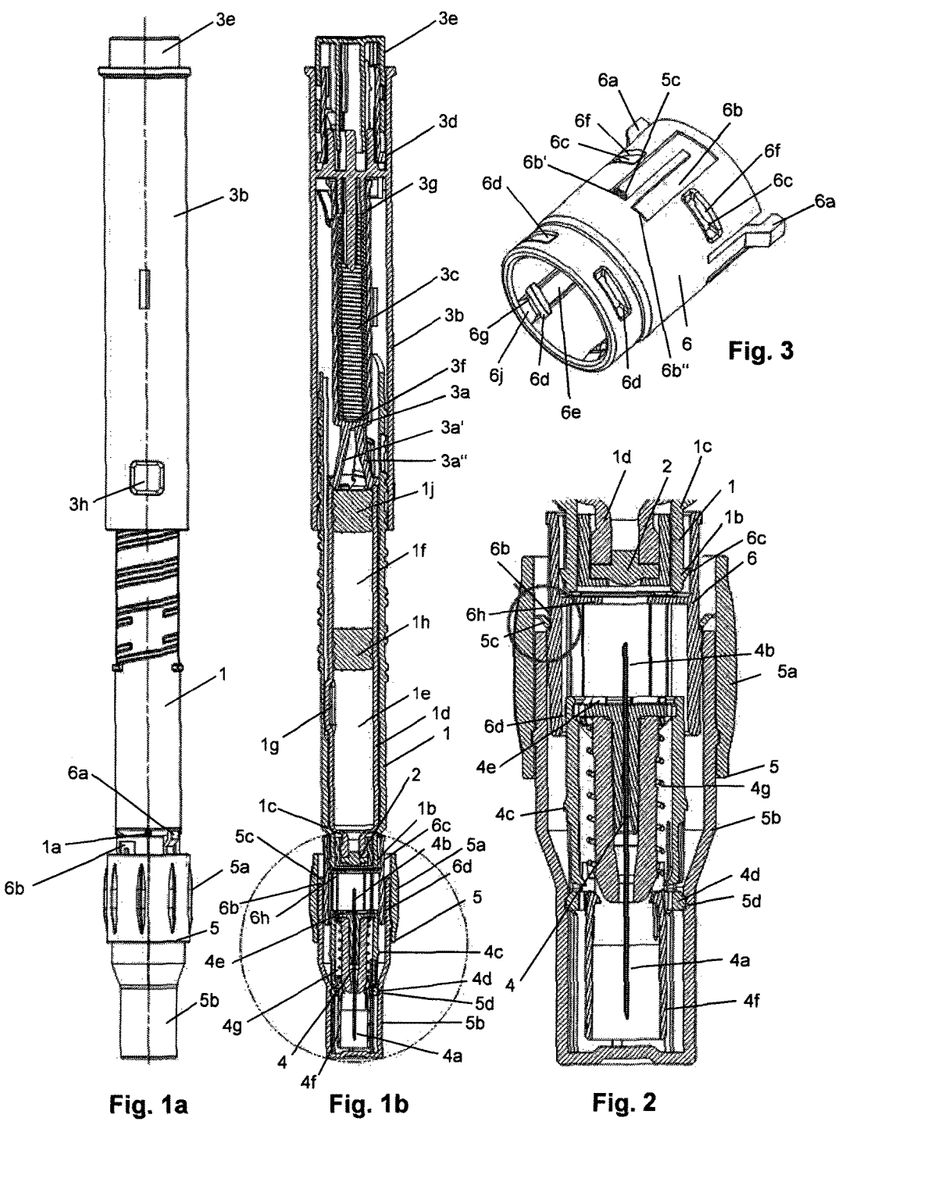
FIG. 1a shows a first embodiment of an administration device, in an initial position, in an external view.
FIG. 1b shows the administration device of the first embodiment, in the initial position, in a longitudinal section.
FIG. 2 shows an enlarged, detailed view in a longitudinal section of an injection needle unit of FIG. 1b, placed on the administration device.
FIG. 3 shows a perspective representation of the position of a locking element of a protective sleeve in a guide mechanism of a guide sleeve of the administration device of the first embodiment, in the initial position.

FIGS. 1a and 1b show a first embodiment of an administration device, in an initial position, in an external view and in a longitudinal section. The administration device comprises a cylindrical cartridge holder (1), in which a cartridge (1d) is supported, and a mixing device for the mixing of an active substance, held in a first chamber (1e) of the cartridge (1d), with a dilution liquid, which is contained in a second chamber (1f) of the cartridge (1d). The chambers (1e, 1f) of the cartridge (1d) can be connected, via a bypass (1g), in a wall of the cartridge (1d). The cartridge (1d) has a first stopper (1h) and a second stopper (1j). The second stopper (1j) seals the cartridge (1d) on the proximal end. On the distal end, the cartridge (1d) exhibits a tapering, whose opening is sealed off by a membrane (2). An injection needle unit (4) is placed on the administration device, on the distal end of the administration device and is connected with the cartridge (1d), via a cylindrical guide sleeve (6) and the cartridge holder (1). A proximal needle portion (4b) of the injection needle unit (4) lies, in the initial position of the administration device, opposite the membrane (2) of the cartridge (1d), wherein the proximal needle portion (4b) protrudes into the guide sleeve (6) on the distal end of the guide sleeve (6). A sleeve-shaped protective sleeve (5) surrounds the injection needle unit (4). The protective sleeve (5) comprises a grip (5a) with longitudinal ribs, which make it possible for the user to have a better grip of the protective sleeve (5), and a protective part (5b), which surrounds the injection needle unit (4), so that the user is protected from an injury with an injection needle of the injection needle unit (4), in particular, a distal needle portion (4a). The grip (5a) and the protective part (5b) of the protective sleeve are axially connected with one another in a firm and nonrotary manner.

The injection needle unit (4) is designed as a safety needle unit, wherein the injection needle unit (4) comprises a protective shield (4f). The protective shield (4f) is situated on the injection needle unit (4) in such a manner that, during the injection, the protective shield can be moved into a proximal position, in which the distal needle portion (4a) is exposed, from a distal position, in which the protective shield (40 surrounds the distal needle portion (4a) for the piercing of the skin. After the injection, the protective shield (4f) can again move into the distal position as a result of an impingement of a spring force of a spring (4g) of the safety needle unit (4), wherein the protective shield (4f) is locked, in a nondetachable manner, by means of a locking device, so as to prevent another injection with the used injection needle unit (4).

A piston rod (3a) and a housing (3b) form the mixing device. The cartridge holder (1) is situated radially between the piston rod (3a) and the housing. The cartridge holder (1) has an outside thread, which is engaged with an inside thread of the housing (3b). The piston rod (3a) is designed in the shape of a sleeve. The piston rod (3a) preferably comprises two holding arms (3a', 3a''), which hold the cartridge (1d) in the cartridge holder (1) in a defined position, relative to the housing (3b). A spring (3c) for the automatic release of the administration device is located on the inside of the piston rod (3a); it is clamped between a distal stop on the bottom of the sleeve (3f) of the piston rod (3a) and a proximal stop on an element (3g), fixed to the housing. Preferably, the administration device can have a release knob (3e) and a blocking ring (3d), wherein the release knob (3e) and the blocking ring (3d) are designed in such a way that the blocking ring (3d) blocks an actuation of the release knob (3e) in the initial position. The blocking ring ensures that the administration device can be released by actuation of the release knob (3e) only after the complete mixing operation and/or priming operation.

Alternatively, the administration device can be released by a manual actuation of the release knob (3e), and that is the reason that the piston rod (3a) does not have a spring (3c). Moreover, alternatively, the administration device cannot have a blocking ring (3d) and/or the piston rod (3a) cannot have holding arms (3a', 3a'') and/or the injection needle unit (4) cannot have a protective shield (4f).

FIG. 2 shows an enlarged, detailed view, in a longitudinal section of the injection needle unit (4), placed on the administration device, in the initial position. The injection needle unit (4) comprises a distal needle portion (4a), turned away from the cartridge holder (1), for piercing the skin and a proximal needle portion (4b), which, in the initial position of the administration device, lies opposite, facing the cartridge holder (1). The injection needle unit (4) is connected with the protective shield (5), in an axially stationary manner, and is preferably nonrotary. To this end, the injection needle unit (4) has a cam or ring (4d), protruding outwards and provided on the outside surface of the jacket; it protrudes into a recess of the annular groove (5d) of the protective shield (5), provided on the inside surface of the jacket. The cartridge holder (1) comprises an opening, provided on the front side, on its distal end, which is situated in the axial alignment to the membrane (2) of the cartridge (1d). The guide sleeve (6) is concentrically situated between the injection needle unit (4) and the protective sleeve (5), wherein the guide sleeve (6) is connected with the proximal end with the cartridge holder (1), in an axially stationary and nonrotary manner. In order to form the axially and nonrotary connection, a recess (6c) is provided in the guide sleeve (6), into which projection (1b), provided on the cartridge holder (1), can lock—especially, a wedge (1b) that projects outward, extending in the circumferential direction. The wedge (1b) can have a steep and a flat flank in such a way that during the installation on the cartridge holder (1), the flat flank of the guide sleeve (6) can be pushed, relative to the cartridge holder (1), over the ramp-shaped proximal end of the cartridge holder (1), until the wedge (1b) of the cartridge holder (1) arrives at the recess (6c) of the guide sleeve (6). The steep flank of the wedge (1b) of the cartridge holder (1) is in a stop contact with a front side of the guide sleeve (6), which is formed by the recess (6c) of the guide sleeve (6). The distal end of the cartridge holder (1) can strike against a proximal side of a counterstop plane (6h) of the guide sleeve (6).

In the initial position, the protective sleeve (5) is connected with the guide sleeve (6) in such a way that it does not rotate, wherein the protective sleeve (5), relative to the guide sleeve (6), can move axially in a sliding contact. The nonrotary connection between the protective sleeve (5) and the guide sleeve (6) can be produced by a stop connection.

The injection needle unit (4) can be held in the guide sleeve (6) so it can move axially. The injection needle unit (4) can move axially in the guide sleeve (6) in such a way that the proximal needle portion (4b) of the injection needle (4), in the initial position of the administration device, is opposite, facing the membrane (2), and in the mixing position is thrust, through the membrane (2), into the container (1). The injection needle unit (4) is guided, via a sliding contact, within the guide sleeve (6) and relative to the guide sleeve (6). The injection needle unit (4) is supported so it can move axially in the guide sleeve, in such a way, that, in the mixing position, the proximal needle portion (4b) can penetrate the membrane (2) of the cartridge (1d), through the opening of the cartridge holder (1), so as to form a fluid connection between the injection needle of the injection needle unit (4) and the cartridge (1d).

In the initial position, the protective sleeve (5), held, in an axially stationary manner, with the injection needle (4), can move only in the proximal direction, relative to the cartridge container (1), held with the cartridge (1d). To this end, the protective sleeve (5) has a locking element (5*c*) that can be clamped, in particular, can be elastically clamped; in the initial position, it interacts, in such a way, with a guide mechanism (6*b*), provided in the guide sleeve (6), that the protective sleeve (5) can move only in the proximal direction, with the injection needle unit (4), held therein, relative to the cartridge holder (1).

In the initial position, the protective sleeve (5) is held tight axially, relative to the guide sleeve (6), via a groove/cam connection—it is held tight axially, especially in the proximal direction. The user can apply a force that exceeds the holding force of the groove/cam connection against the protective sleeve (5), in the proximal direction. The groove/cam connection is loosened and the protective sleeve (5), held with the injection needle unit (4), can be moved, relative to the cartridge holder (1), in the proximal direction. A relative movement between the protective sleeve (5) and the guide sleeve (6) in the distal direction is prevented by the stop contact between the locking element (5*c*) of the protective sleeve (5) and the guide mechanism (6*b*) of the guide sleeve (6).

FIG. 3 shows the guide sleeve (6) in interaction with the locking element (5*c*) of the protective sleeve (5) in the initial position. The locking element (5*c*) of the protective sleeve (5) engages the guide mechanism (6*b*) of the guide sleeve (6). The guide mechanism (6*b*) is designed in the shape of a U and has a steep front edge (6*b*') on one end, wherein the other end is designed in the shape of a ramp. The locking element (5*c*) is shaped as a bendable flap, in particular, a flap that can bend elastically. A stop surface (5*c*') of the locking element (5*c*) can form a stop contact with the steep front edge (6*b*') of the guide mechanism (6*b*) of the guide sleeve (6) in the initial position, so as to prevent that, in the initial position, the protective sleeve (5) can be moved with the injection needle (4) in the distal direction, in particular, that it can be removed from the injection needle unit (4).

At least one snap arm (6*a*) that can be clamped inwards is provided on the proximal end of the guide sleeve (6). The snap arm (6*a*) is designed in the shape of a heel and protrudes outwards from the outside jacket surface of the guide sleeve (6).

The recess (6*c*) of the guide sleeve (6), which can interact with the wedge (1*b*) of the cartridge holder (1), so as to form an axially stationary and nonrotary connection between the guide sleeve (6) and the cartridge holder (1), is designed in the form of a slit. The inside surface of the jacket of the guide sleeve (6) has a longitudinal crosslink (6*e*) that protrudes inwards, wherein the slit-shaped recess (6*c*) is located in the area of the longitudinal crosslink (6*e*). The wedge (1*b*) that protrudes outwards and extends in the circumferential direction is placed on the cartridge holder (1). In order to ensure an axially stationary and nonrotary connection between the guide sleeve and the cartridge holder (1), the steep side of the wedge (1*b*) can protrude in the direction of the recess (6*c*), on the one hand, and impact against the stop surface (6*f*), formed by the longitudinal crosslink (6*e*) and the recess (6*c*), and the distal end of the cartridge holder (1) can impact against the proximal side of the counterstop plane (6*h*) of the guide sleeve (6), on the other hand.

The guide sleeve (6) has an additional recess (6*d*), in axial alignment to the proximal recess (6*c*), which, with the surrounding wedge (1*b*) of the cartridge holder (1), is used for the axial and rotary securing of the guide sleeve (6) with the cartridge holder (1). The two recesses (6*c*, 6*d*) are designed essentially the same. The recess (6*d*), which is provided on the distal end of the guide sleeve (6), makes possible an axially stationary connection of the injection needle unit (4) with the guide sleeve (6), if the injection needle unit is in the mixing position, wherein a projection (4*c*) that protrudes outwards on the injection needle unit (4) arrives at the distal recess (6*d*) of the guide sleeve (6).

The longitudinal crosslink (6*e*), placed on the inside of the jacket of the guide sleeve (6), is in sliding contact with the injection needle unit, wherein the injection needle unit (4) can move relative to the guide sleeve (6). The sliding contact between the guide sleeve (6) and the injection needle unit (4) is used for the longitudinal guiding of the injection needle (4), held by the protective sleeve (5), from the initial position—in which the proximal needle portion (4*b*) of the injection needle unit (4) lies opposite, facing the membrane (2) of the cartridge (1*d*)—into the mixing position, in which the proximal needle portion (4*b*) is thrust, through the membrane (2), into the cartridge (1*d*).

Figures 4, 9:
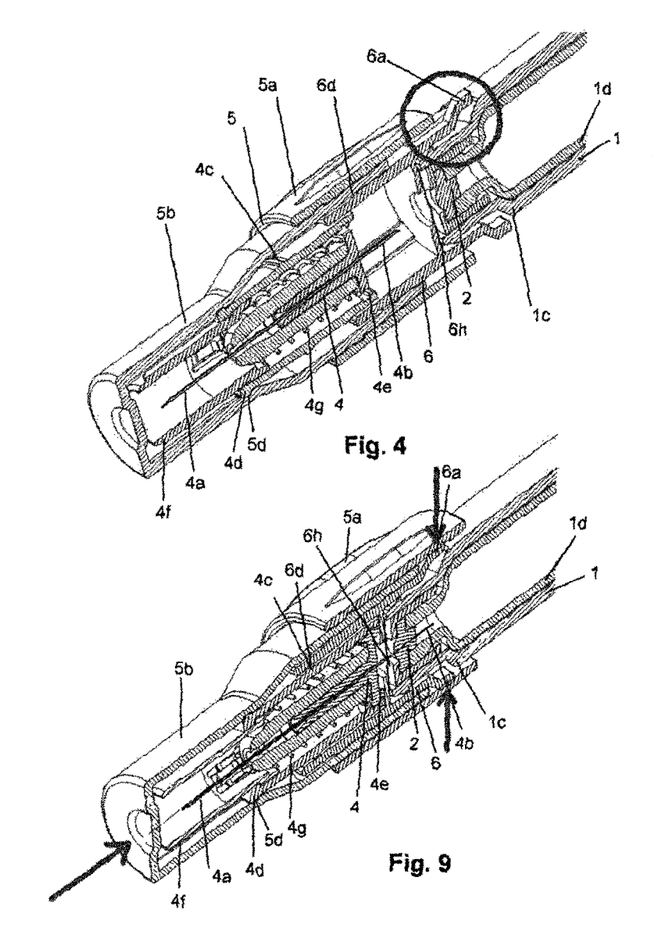
FIG. 4 shows an enlarged, perspective top view, in a longitudinal section of the injection needle of FIG. 1b, placed on the administration device.
FIG. 9 shows an enlarged, perspective, detailed view, in a longitudinal section of the injection needle unit of FIG. 6b, placed on the administration device.
Figure 5:
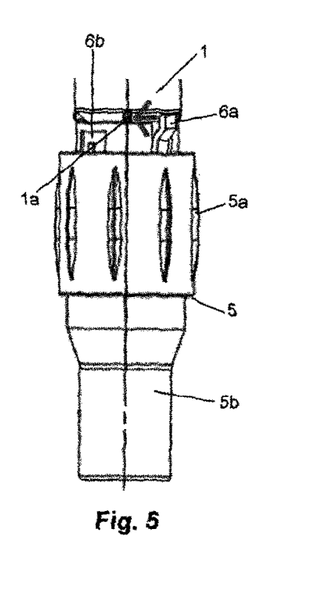
FIG. 5 shows an enlarged, perspective detailed view, in an external view of the injection needle unit of FIG. 1b, placed on the administration device.

FIG. 4 shows an enlarged, perspective, detailed view, in a longitudinal section of the injection needle, placed on the administration device, in the initial position. The elastically clampable snap arm (6*a*) of the guide sleeve 6 is situated radially relaxed between the cartridge holder (1) and the protective sleeve (5), especially, the grip (5*a*) of the protective sleeve (5), and protrudes beyond the proximal end of the grip (5*a*) of the protective sleeve (5), in the longitudinal direction of the administration device. As shown in FIG. 5, a projection provided on the cartridge holder (1), especially, a cam (1*a*), is provided in the circumferential direction, staggered, relative to the snap arm (6*a*) of the guide sleeve (6). The protective sleeve (5) can be rotated, relative to the administration device, in particular, the mixing device, wherein the guide sleeve (6), which is connected so it cannot rotate with the protective sleeve (5), is also rotated in the initial position. The locking element (5*c*) of the protective sleeve (5) strikes a flank of the guide mechanism (6*b*) of the guide sleeve (6) and forms the nonrotary connection between the protective sleeve (5) and the guide sleeve (6). The relaxed snap arm (6*a*) of the guide sleeve (6) does not arrive at a rotation of the protective sleeve in a stop contact with the cam (1*a*) of the cartridge holder (1), since the relaxed snap arm (6*a*) is at a distance radially from the cam (1*a*). Consequently, the cartridge holder (1) cannot be screwed into the housing (3*b*) of the administration device, via the stop contact, between the cam (1*a*) of the cartridge holder (1) and the snap arm (6*a*) of the guide sleeve (6), so as to mix the active substance with the dilution liquid in the cartridge (1*d*).

Figures 6A, 6B, 7, 8:
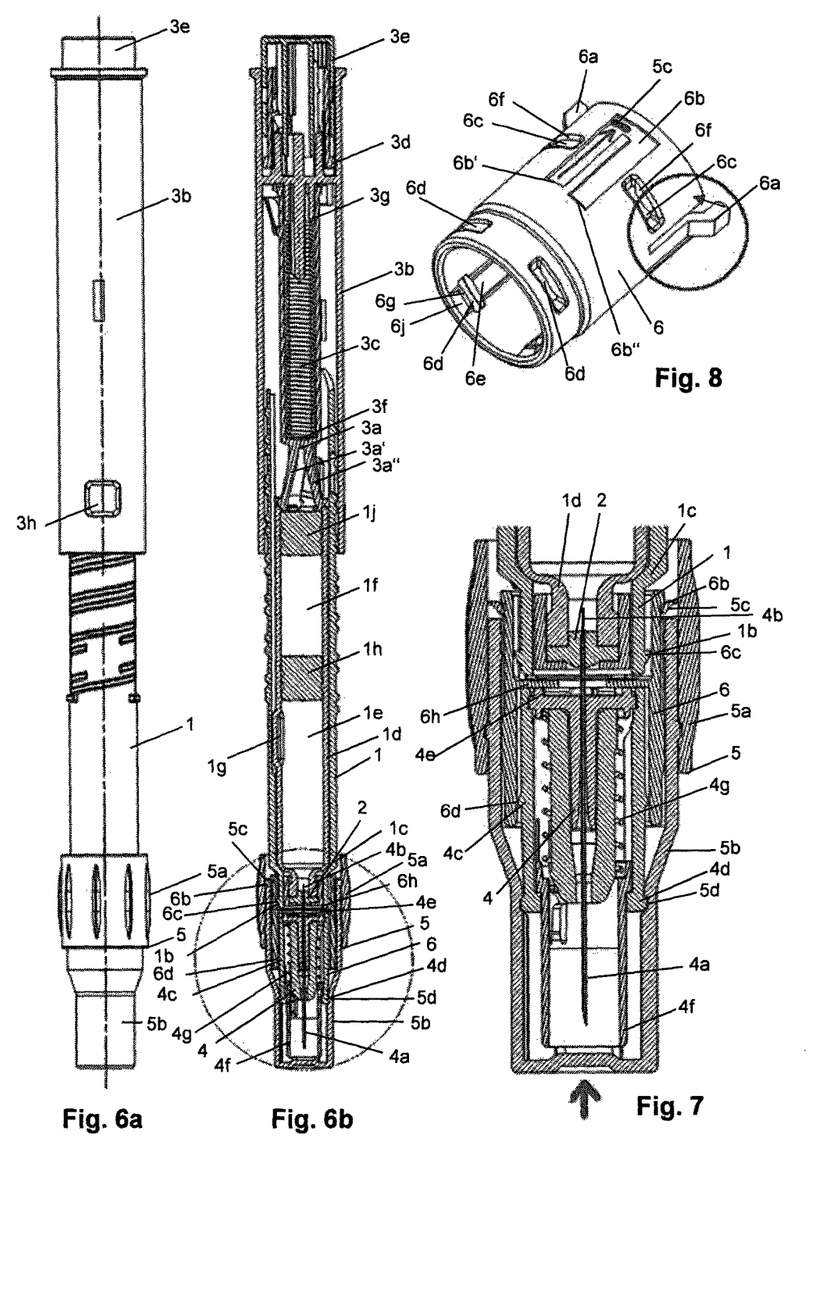
FIG. 6a shows the administration device of the first embodiment, in a piercing position, in an external view.
FIG. 6b shows the administration device of the first embodiment, in the piercing position, in a longitudinal section.
FIG. 7 shows an enlarged detailed view, in a longitudinal section of the injection needle unit of FIG. 6b, placed on the administration device.
FIG. 8 shows a perspective representation of the position of the locking element of the protective sleeve in the guide mechanism of the guide sleeve of the administration device of the first embodiment, in the piercing position.

FIGS. 6*a* and 6*b* show the administration device of the first embodiment in a piercing position, in an outside view and in a longitudinal section, wherein FIG. 7 shows an enlarged, detailed view in a longitudinal section of the injection needle unit (4) of FIG. 6*b*, placed on the administration device. In the initial position, the protective sleeve (5), held with the injection needle unit (4), can be moved only in the proximal direction because of the stop contact between the locking element (5*c*) of the protective sleeve (5) and the steep front edge (6*b*') of the guide mechanism (6*b*) of the guide sleeve (6). To this end, the user presses the protective sleeve (5) in the proximal direction, relative to the mixing device, in order to arrive at the piercing position. The protective sleeve (5) moves with the injection needle unit (4), connected in an axially stationary manner, in a sliding contact, relative to the guide sleeve (6), until the injection needle element (4), with a stop cam or a stop ring (4*e*), impacts a distal side of the counter stop plane (6*h*) of the guide sleeve (6), which lies on the distal end of the cartridge holder (1). If the injection needle unit (4) lies on the distal side of the counterstop plane (6) of the guide sleeve (6), the proximal portion (4b) of the injection needle unit (4) penetrates the opening of the cartridge holder (1) as well as the membrane (2) of the cartridge (1d), wherein a fluid connection is present between the injection needle of the injection needle unit (4) and the cartridge (1d).

The projection (4c), protruding outwards on the injection needle unit (4), has a steep flank in the distal direction and a flat flank in the proximal direction. The projection (4c) can be designed as a surrounding wedge, situated on the outside surface of the jacket of the injection needle unit (4). During the movement into the mixing position, the flat flank of the projection (4c) slides, via the ramp (6j) of the guide sleeve (6), until the projection (4c) arrives at the distal recess (6c) of the guide sleeve (6). The injection needle unit (4) is axially connected with the guide sleeve, since the steep flank of the projection (4c) impacts against a stop surface (6g) of the recess (6c) and the stop cam or the stop ring (4e) of the injection needle unit (4) strikes the distal side of the counterstop plane (6h) of the guide sleeve (6).

FIG. 8 shows the position of the locking element (5c) of the protective sleeve (5) in the guide mechanism (6b) of the guide sleeve (6) in the piercing position. The locking element (5c) arrives at the proximal position, along the guide mechanism (6b). If, in this position, the user would like to remove the protective sleeve (5) from the injection needle unit (4), without carrying out a mixing operation, the locking element (5c) of the protective sleeve moves in the distal direction, relative to the guide sleeve (6), until the locking element (5c) strikes the steep front edge (6b') of the guide sleeve (6). Thus, the protective sleeve (5) cannot be removed from the injection needle unit (4) without a mixing operation.

As a result of the axial movement of the protective sleeve (5), firmly connected, axially, with the injection needle unit (4), in the proximal direction, relative to the guide sleeve (6), the snap arm (6a), provided on the guide sleeve (6), is clamped radially inwards, as shown in FIG. 9. With the axial movement, the inside surface of the jacket of the protective sleeve slides over the snap arm (6a) and presses the snap arm (6) radially inwards.

Figures 10A, 10B:
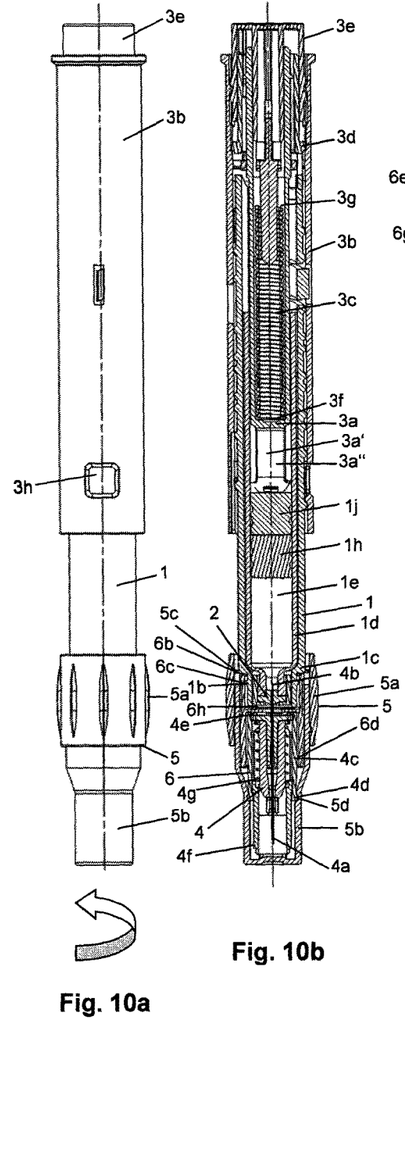
FIG. 10a shows the administration device of the first embodiment, in the mixing position, in an external view.
FIG. 10b shows the administration device of the first embodiment, in the mixing position, in a longitudinal section.
Figure 11:
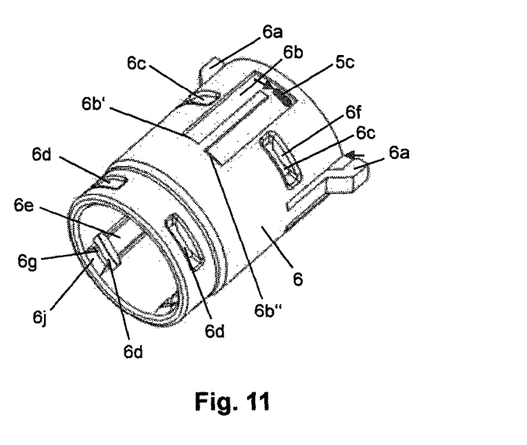
FIG. 11 shows a perspective representation of the position of the locking element of the protective sleeve in the guide mechanism of the guide sleeve of the administration device of the first embodiment, in the mixing position.

FIGS. 10a and 10b show the administration device of the first embodiment in a mixing position, in an outside view and in a longitudinal section. For the mixing, the protective sleeve (5) is rotated relative to the mixing device of the administration device. To this end, the user grabs the grip (5a) of the protective sleeve (5) and rotates the protective sleeve (5), relative to the housing (3b). As shown in FIG. 11, the protective sleeve (5) is thereby rotated, relative to the guide sleeve (6), until the locking element (5c) of the protective sleeve arrives at the guide mechanism (6b), in a stop contact with a flank of the guide mechanism (6b) of the guide sleeve (6). With an additional rotation of the protective sleeve (5), the locking element (5c) moves along the guide sleeve (6), until the snap arm (6a) of the guide sleeve (6) impacts the cam (1a) of the cartridge holder (1). The protective sleeve (5) is connected in a nonrotary manner, via the guide sleeve (6), with the cartridge holder (1) in at least one rotary direction, wherein the locking element (5c) of the protective sleeve is in a stop contact with the flank of the guide mechanism (6b) of the guide sleeve (6) and the snap arm (6a) of the guide sleeve (6) in a stop contact with the cam (1a) of the cartridge holder (1). As a result of the nonrotary connection between the protective sleeve and the cartridge holder (1), the active substance can be mixed with the dilution liquid for the active substance by a rotation of the protective sleeve (5), relative to the mixing device, namely, the housing (3b) and the piston rod (3a). The cartridge holder (1) is screwed in between the housing (3b) and the piston rod (3a), wherein the piston rod (3a) impacts the two stoppers (1j) of the cartridge (1d) with the two holding arms (3a', 3a''). To screw in the cartridge holder (1), an inside thread is provided on the inside of the housing 93b) and an outside thread, on the outside of the cartridge container (1). As a result of the transfer of force of the dilution liquid between the second and the first stoppers (1j, 1h), the two stoppers (1h, 1j) are pushed in the distal direction within and relative to the cartridge (1d), until the first stopper (1h) comes to lie on the bypass (1g), through which the dilution liquid can flow into the first chamber (1e), and the second stopper (1j) comes to lie on the first stopper (1h). In the mixed position, the active substance of the first chamber (1e) is mixed with the dilution liquid of the second chamber (1f). The end of the mixing can be indicated by a tactile, acoustic, and/or visual signal of a display device (3h). With an additional slight rotation of the cartridge container (1), a priming operation can be carried out, wherein this operation leads to another movement forward of the two stoppers (1h, 1j), so that a gas contained in the cartridge (1d) and/or in the injection needle can escape from the injection needle, until a slight quantity of mixed active substances exits from the injection needle of the injection needle unit (4). The conclusion of the priming operation can be indicated by a tactile, acoustic, and/or visual signal of the display device (3h). With the last screwing movement of the cartridge container (1) into the housing (3b), the blocking ring (3d) can be moved from the blocking position into a release position. By a rotation, a stop of the cartridge holder (1) can move along the blocking ring (3d), so that it is rotated, relative to the housing (3b) and the release knob (3e). By this rotary movement, the blocking ring (3d) is moved from the blocking position into the release position. In the release position, the release knob (3e) can be actuated in that, relative to the housing (3b), the release knob (3e) can be pressed into the housing (3b), along the longitudinal axis.

Figure 12A:
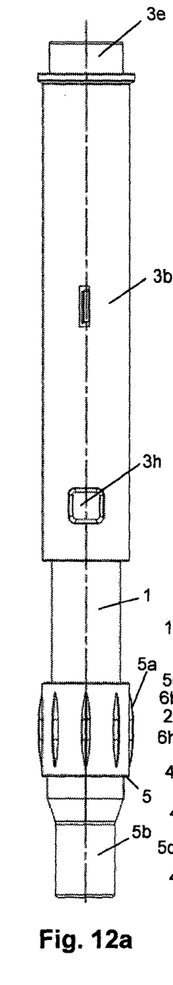
FIG. 12a shows the administration device of the first embodiment, in the mixed and/or primed position, in an external view, wherein the protective sleeve can be removed from the injection needle unit.
Figure 12B:
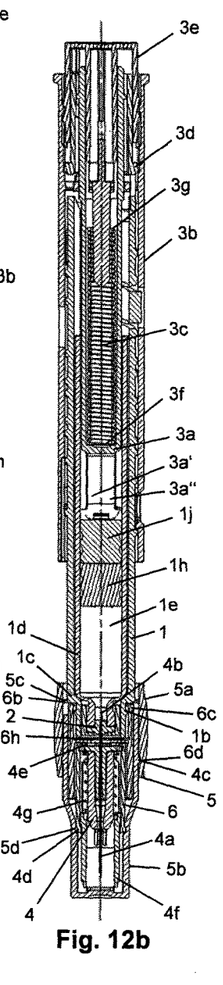
FIG. 12b shows the administration device of the first embodiment, in the mixed and/or primed position, in a longitudinal section, wherein the protective sleeve can be removed from the injection needle unit.
Figure 13:
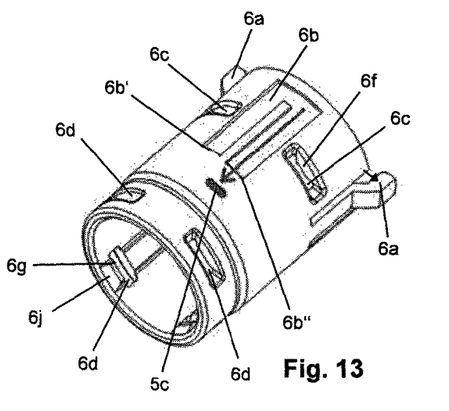
FIG. 13 shows a perspective representation of the position of the locking element of the protective sleeve, in the guide mechanism of the guide sleeve of the administration device of the first embodiment, during the removal of the protective sleeve from the injection needle unit.

FIGS. 12a and 12b show the administration device of the first embodiment in the mixed and/or primed position, in an outside view and in a longitudinal section, wherein the protective sleeve (5) can be removed from the injection needle unit (4). FIG. 13 shows the position of the locking element (5c) of the protective sleeve (5) in the guide mechanism (6b) of the guide sleeve (6) of the administration device when the protective sleeve (5) is removed from the injection needle unit (4). The locking element (5c) is in a stop contact with the flank of the guide mechanism (6b) after a relative rotation of the protective sleeve (5) to the guide sleeve (6). If the protective sleeve (5) is moved, relative to the guide sleeve (6), in the distal direction, the locking element (5c) of the protective sleeve (5) slides, along the guide mechanism (6c), over the ramp (6b'') of the guide sleeve (6). The protective sleeve (5) can be removed from the injection needle unit (4).

Figures 14A, 14B:
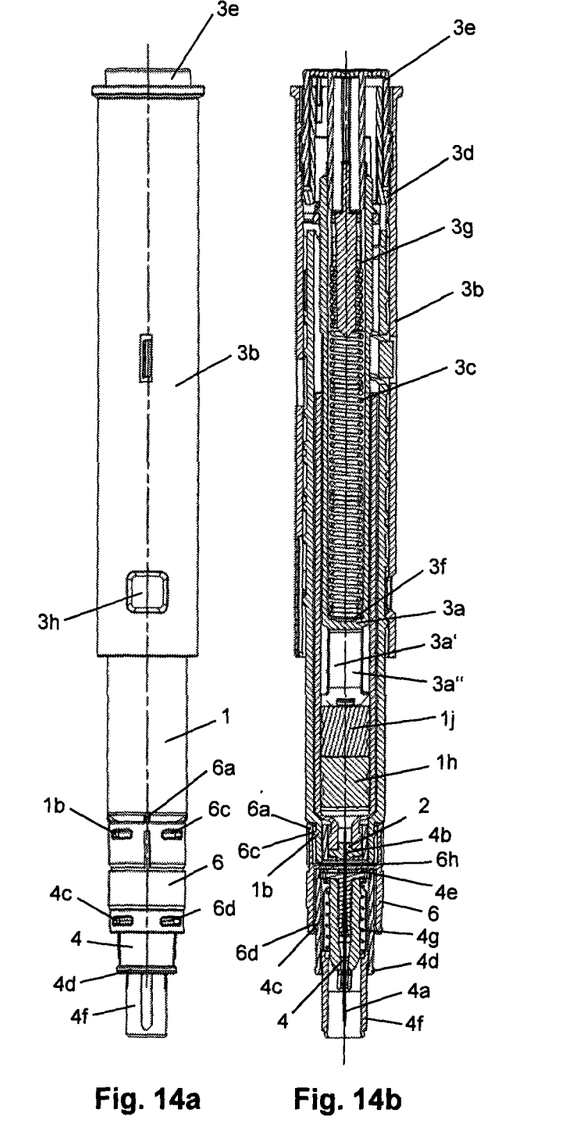
FIG. 14a shows the administration device of the first embodiment, in the shaken out state, in an external view.
FIG. 14b shows the administration device of the first embodiment, in a shaken-out state, in a longitudinal section.

FIGS. 14a and 14b show the administration device of the embodiment in an emptied state, in an outside view and in a longitudinal section. To release the administration device, the release knob (3e) can be pressed, relative to the housing (3b), along the longitudinal axis into the housing (3b). The release knob (3e) is designed in such a manner that the release knob (3e) releases a securing of the piston rod (3a) on a housing element when the release knob (3e) is moved forward. When released, the spring force of the spring (3c) begins to act and presses against the piston rod (3a). The piston rod (3a) is pushed by the force of the spring (3c), relative to the cartridge (1d), wherein the holding arms (3a', 3a″) of the piston rod (3a) drive the stoppers (1j, 1h) within the cartridge (1d), so that the mixed active substance is emptied from the first chamber (1e). The spring (3c) pushes the piston rod (3a) into the cartridge (1d) until a projection, which is provided on the piston rod (3a), strikes an edge of the housing (3b). As soon as the projection strikes the housing (3b), the emptying of the mixed active substance has ended. A tactile, acoustic, and/or visual signal of the display device (3h) can indicate that the emptying has ended.

After the injection into the skin, the protective sleeve (5) can again be placed on the injection needle unit (4). The protective sleeve (5) can be moved, relative to the guide sleeve (6), in the proximal direction, until the groove/cam connection is again established between the protective sleeve (5) and the guide sleeve (6). The cartridge holder, held with the cartridge, can be uncoupled, with the injection needle unit, from the administration device, in order to couple a cartridge holder with a new cartridge.

Alternatively, the used administration device can be disposed of after the injection.

Figure 15A:
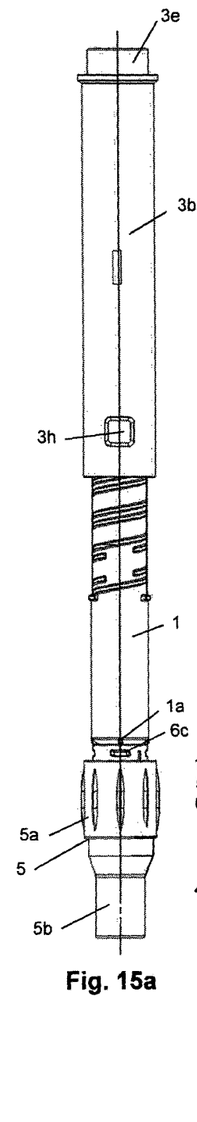
FIG. 15a shows a second embodiment of an administration device, in an initial position, in an external view.
Figure 15B:
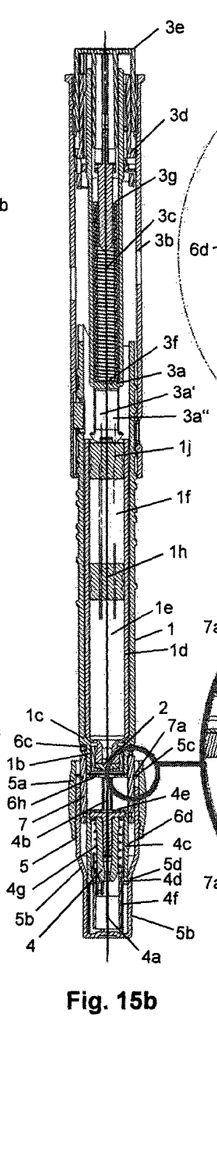
FIG. 15b shows the administration device of the second embodiment, in the initial position, in a longitudinal section.
Figure 16:
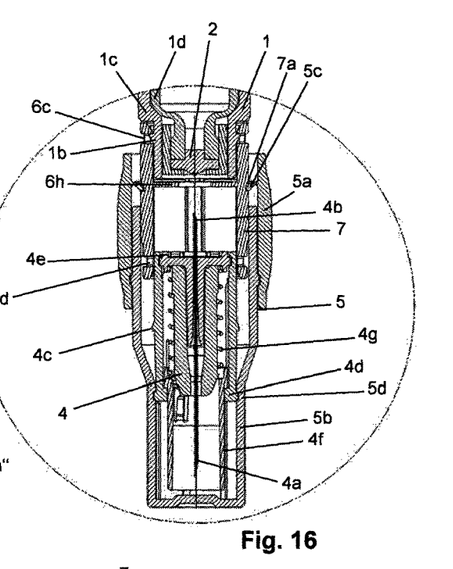
FIG. 16 shows an, enlarged, detailed view, in a longitudinal section of an injection needle unit of FIG. 15b, placed on the administration device.
Figure 17:
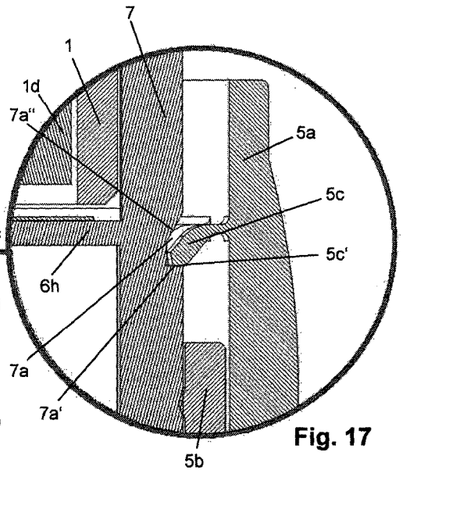
FIG. 17 shows an enlarged, detailed view, in a longitudinal section of the intrusion between a locking element of a protective sleeve and a recess of a guide sleeve, in the initial position of the injection needle unit of FIG. 15b, placed on the administration device.

In an initial position, FIGS. 15a and 15b show the administration device of a second embodiment, in an outside view and in a longitudinal section. The administration device essentially differs from the administration device of the first embodiment example only with reference to the design of the guide sleeve (7), with reference to the interaction of the guide sleeve (7) with the locking element (5c), and with reference to the interaction of the locking element (5c) with the cartridge container (1). FIG. 16 shows an enlarged, detailed view, in a longitudinal section of the injection needle unit (4) of FIG. 15b, placed on the administration device. And FIG. 17 shows an enlarged, detailed view, in a longitudinal section of the intrusion between the locking element (5c) of the protective sleeve (5) and a recess (7a) of the guide sleeve (7), in the initial position of the injection needle unit (4) of FIG. 15b, placed on the administration device. The guide sleeve (7) can be connected with the protective sleeve (5), via a nonrotary ribbed connection. Alternatively, the recess (7a) of the guide sleeve (7) and the locking element (5c) can be designed in such a way that the guide sleeve (7) is connected, in a nonrotary manner, with the protective sleeve (5)—at least in the initial position. The recess (7a) in the guide sleeve (7) has a steep edge (7a′) and a flat edge (7a″). The locking element (5c) is designed in such a manner that, in the initial position, it impacts with the stop surface (5c′) against the steep edge (7a′) of the guide sleeve (7), so as to prevent the protective sleeve (5) with the held injection needle unit (4) from being movable in the distal direction, relative to the guide sleeve (7)—in particular, from it being possible to remove the protective sleeve from the injection needle unit (4). In the initial position, the protective sleeve (5) is firmly held axially, relative to the guide sleeve (7), via a groove/cam connection—in particular, it is firmly held axially, in the proximal direction. The user can apply a force in the proximal direction, against the protective sleeve (5), which exceeds the holding force of the groove/cam connection. The groove/cam connection is loosened and the protective sleeve (5), held with the injection needle unit (4), can be moved, relative to the cartridge container (1), in the proximal direction, until the injection needle unit, with the stop cam or the stop ring (4e), impacts the distal side of the counterstop plane (6h) of the guide sleeve (6), which lies on the distal end of the cartridge holder (1). The locking element (5c), which is designed in a deformable manner, in particular, in an elastically clampable manner, slides thereby, relative to the guide sleeve (7) over the flat edge (7a″) of the guide sleeve (7), from the recess (7a), onto the outside surface of the jacket of the guide sleeve (7). The locking element (5c) is thereby under even more tension. The protective sleeve (5) and the injection needle unit (4) thereby move, in a sliding contact, with the guide sleeve. The protective sleeve (5), with the injection needle unit (4) held therein, moves, relative to the guide sleeve (7), in the proximal direction. With the movement in the proximal direction, the injection needle of the injection needle unit (4) penetrates the membrane of the cartridge (1d). The locking element (5c) slides over the proximal end of the guide sleeve (7) and can relax, in particular, relax elastically, between the recess formed by the shoulder (1c) of the cartridge holder (1) and the recess formed by the proximal end of the guide sleeve (7).

Figure 18A:
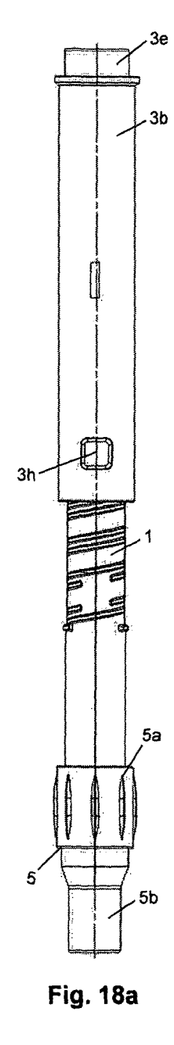
FIG. 18a shows the administration device of the second embodiment, in a mixing position, in an external view.
Figure 18B:
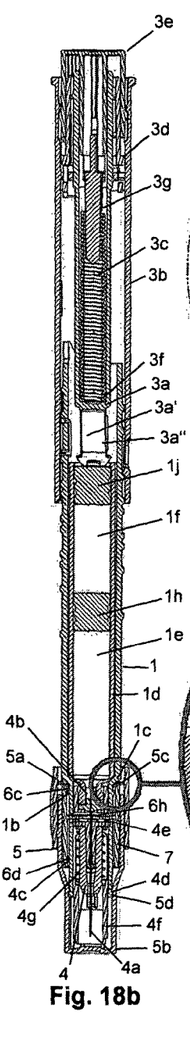
FIG. 18b shows the administration device of the second embodiment, in the mixing position, in a longitudinal section.
Figure 19:
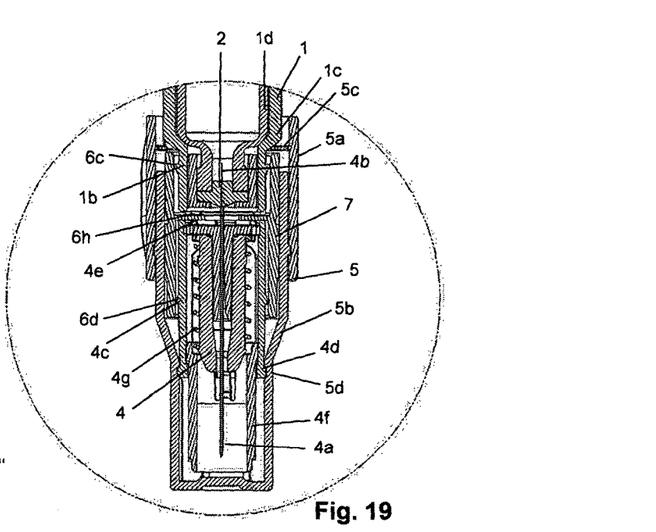
FIG. 19 shows an enlarged, detailed view, in a longitudinal section of the injection needle unit of FIG. 18b, placed on the administration device.
Figure 20:
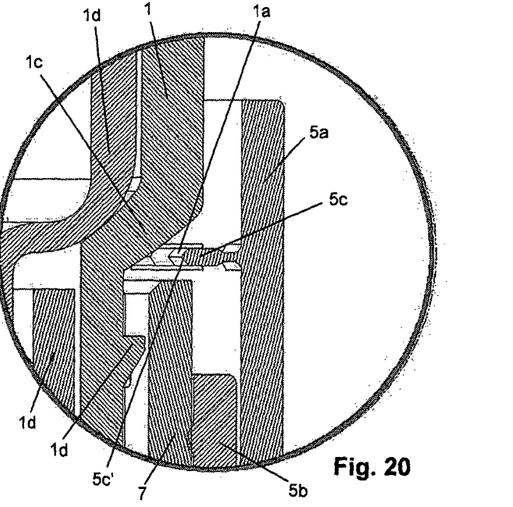
FIG. 20 shows an enlarged, detailed view, in a longitudinal section of the intrusion between the locking element of the protective sleeve and the projection of the cartridge holder, in the mixing position of the injection needle unit of FIG. 18b, placed on the administration device.

FIGS. 18a and 18b show the administration device of the second embodiment in a mixing position, in an outside view and in a longitudinal section. FIG. 19 shows an enlarged, detailed view in a longitudinal section of the injection needle unit (4) of FIG. 18b, placed on the administration device. FIG. 20 depicts an enlarged, detailed view, in a longitudinal section of the intrusion between the locking element (5c) of the protective sleeve (5) and the projection (1a), placed on the cartridge holder, in particular, a cam (1a), in the mixing position of the injection needle unit of FIG. 18b, placed on the administration device. With a rotation of the protective sleeve (5), relative to the cartridge holder (1d), so as to mix the active substance with the dilution liquid, the relaxed—in particular, elastically relaxed—locking element (5c) of the protective sleeve (5) can impact a projection (1a), provided on the cartridge holder, in particular, a cam (1a). Via the nonrotary connection between the protective sleeve (5), in particular, the locking element (5c), and the cartridge holder (1), in particular, a cam (1a), the cartridge holder (1) can be conducted into the housing (3b), in a thread engagement with the housing (3b). If the mixing operation has ended, the protective sleeve (5) can be removed from the injection needle unit (4) in that the protective sleeve (5) is moved, relative to the cartridge holder (1), in the distal direction. As a result of its deformability, in particular, its elastic clamping capacity, the locking element (5c) can be clamped via the proximal end of the cartridge holder (1), in that the locking element (5c) slides over the proximal end of the cartridge holder (1), relative to the cartridge holder (1). The locking element (5c) slides on the outside surface of the jacket of the guide sleeve (7), relative to the guide sleeve (7), via the recess of the guide sleeve (7). The protective sleeve (5) can thus be removed from the injection needle unit (4).

We claim:

1. An administration device for the administration of a fluid active substance from a container, comprising:
   a) a container with at least one first chamber with an active substance and a second chamber with a dilution liquid for the active substance, wherein the container has a membrane for sealing on one end;
   b) a mixing device for the mixing of the active substance with the dilution liquid for the active substance;
   c) an injection needle unit, which has a distal needle portion facing away from the container for piercing the skin, and a proximal needle portion, which, in an initial position of the administration device, lies opposite, facing the membrane, and which in a mixing position is thrust through the membrane into the container,
   wherein the administration device comprises a protective sleeve, which is situated coaxially around the injection needle unit and is movable in the proximal direction, relative to the container, with the injection needle unit held by the protective sleeve, wherein the protective sleeve is connected with the container in a nonrotary manner, and in the mixing position, the protective sleeve is rotatable relative to the mixing device so as to radially screw the container and cause the active substance to be mixed with the dilution liquid, wherein the administration device further comprises a guide sleeve and the guide sleeve is situated radially between the injection needle unit and the protective sleeve and is firmly connected, axially, with the container on a proximal end of the guide sleeve, wherein the protective sleeve has a clampable locking element, which, in the initial position, interacts with the guide sleeve in such a way that the protective sleeve is movable with the injection needle unit held therein relative to the container in the proximal direction, and wherein the clampable locking element of the protective sleeve interacts, in the mixing position, with the guide sleeve in such a way that the protective sleeve is movable, relative to the container, in the distal direction.

2. The administration device according to claim 1, wherein the injection needle unit is held axially in the guide sleeve so that the injection needle unit is movable relative to the guide sleeve.

3. The administration device according to claim 1, wherein the protective sleeve in the initial position is rotatable relative to the container.

4. The administration device according to claim 1, wherein the guide sleeve is rotatable, relative to the container, in the initial position or in the mixing position.

5. The administration device according to claim 1, the protective sleeve does not rotate, relative to the guide sleeve, in the initial position or in the mixing position.

6. The administration device according to claim 1, wherein the guide sleeve has a guide mechanism and the clampable locking element is guided along the guide mechanism.

7. The administration device according to claim 1, wherein the guide sleeve has a guide mechanism and a clampable locking element is guided along the guide mechanism.

8. The administration device according to claim 1, wherein the nonrotary connection between the protective sleeve and the container is brought about, in the mixing position, by an intrusion between the container and a part of the protective sleeve or the clampable locking element of the protective sleeve.

9. The administration device according to claim 8, wherein the container and the part of the protective sleeve or the clampable locking element of the protective sleeve form a form-locking or force-locking intrusion.

10. The administration device according to claim 1, wherein the nonrotary connection between the protective sleeve and the container is brought about, in the mixing position, by an intrusion between the container and a snap arm situated on the guide sleeve.

11. The administration device according to claim 10, wherein the snap arm is clamped radially inwards in the mixing position.

12. The administration device according to claim 10, wherein the snap arm acts, in the mixing position, against a projection placed on the container and forms the intrusion between the container and the snap arm.

13. The administration device according to claim 10, wherein the intrusion is a ribbed connection, groove/wedge connection, pin/borehole connection, stop connection, or snap connection.

14. The administration device according to claim 1, wherein the nonrotary connection between the protective sleeve and the container can be brought about, in the mixing position, by an intrusion between the container and a part of the protective sleeve or the clampable locking element of the protective sleeve.

15. The administration device according to claim 14, wherein the container and the part of the protective sleeve or the clampable locking element of the protective sleeve form a form-locking or force-locking intrusion.

16. The administration device according to claim 14, wherein the intrusion is a ribbed connection, groove/wedge connection, pin/borehole connection, stop connection, or snap connection.

17. An administration device for the administration of a fluid active substance from a container, comprising:
a) a container with at least one first chamber with an active substance and a second chamber with a dilution liquid for the active substance, wherein the container has a membrane for sealing on one end;
b) a mixing device for the mixing of the active substance with the dilution liquid for the active substance;
c) an injection needle unit, which has a distal needle portion facing away from the container for piercing the skin, and a proximal needle portion, which, in an initial position of the administration device, lies opposite, facing the membrane, and which in a mixing position is thrust through the membrane into the container;
d) a protective sleeve, which is situated coaxially around the injection needle unit and is movable in the proximal direction, relative to the container, with the injection needle unit held by the protective sleeve, wherein the protective sleeve is connected with the container, in a nonrotary manner, and in the mixing position, the protective sleeve is rotatable relative to the mixing device so as to radially screw the container and cause the active substance to be mixed with the dilution liquid, and wherein the protective sleeve has a clampable locking element; and
e) a guide sleeve, wherein the clampable locking element, in the mixing position, interacts with the guide sleeve in such a way that the protective sleeve is movable, relative to the container, in the distal direction.

* * * * *